(12) United States Patent
Clement et al.

(10) Patent No.: US 9,062,054 B2
(45) Date of Patent: Jun. 23, 2015

(54) PYRIDO [3,4-C] [1,9] PHENANTHROLINE AND 11, 12 DIHYDROPYRIDO [3,4-C] [1,9] PHENANTHROLINE DERIVATIVES AND THE USE THEREOF, PARTICULARLY FOR TREATING CANCER

(71) Applicant: CHRISTIAN-ALBRECHTS-UNIVERSITAET ZU KIEL, Kiel (DE)

(72) Inventors: Bernd Clement, Kiel (DE); Christopher Meier, Kiel (DE); Dieter Heber, Molfsee (DE); Lars Stenzel, Oyten (DE)

(73) Assignee: CHRISTIAN-ALBRECHTS-UNIVERSITAET ZU KIEL, Kiel (DE)

( * ) Notice: Subject to any disclaimer, the term of this patent is extended or adjusted under 35 U.S.C. 154(b) by 0 days.

(21) Appl. No.: 14/390,661

(22) PCT Filed: Apr. 5, 2013

(86) PCT No.: PCT/EP2013/057212
§ 371 (c)(1),
(2) Date: Oct. 3, 2014

(87) PCT Pub. No.: WO2013/150140
PCT Pub. Date: Oct. 10, 2013

(65) Prior Publication Data
US 2015/0099774 A1  Apr. 9, 2015

(30) Foreign Application Priority Data
Apr. 5, 2012  (DE) .......................... 10 2012 006 903

(51) Int. Cl.
*C07D 471/14* (2006.01)
*A61K 31/4745* (2006.01)
*A61P 29/00* (2006.01)
*A61P 31/00* (2006.01)
*A61P 31/04* (2006.01)
*A61P 31/10* (2006.01)
*A61P 31/12* (2006.01)
*A61P 33/00* (2006.01)
*A61P 35/00* (2006.01)

(52) U.S. Cl.
CPC .................................. *C07D 471/14* (2013.01)

(58) Field of Classification Search
None
See application file for complete search history.

(56) References Cited

FOREIGN PATENT DOCUMENTS

WO  WO-97/14683 A2  4/1997

OTHER PUBLICATIONS

International Search Report for International Application No. PCT/EP2013/057212, mailed Jun. 14, 2013 (3 pages).
Kock et al., "Synthesis and biological evaluation of 11-substituted 6-aminobenzo[c]phenanthridine derivatives, a new class of antitumor agents," J Med Chem. 48(8):2772-7 (2005).
Meier et al. "Synthesis and physicochemical characterization of novel 6-aminopyrido [3,4-c] [1,9] phenanthrolines as aza-analogs of benzo[c]phenanthridines," Tetrahedron. 68(44):9105-12 (2012).
Stenzel, Lars, "Synthese neuer Benzo[c]phenanthridin-Derivate und deren Stickstoff-Analoga als petentielle Zytostatika," Dissertation, Christian-Albrechts-Universität zu Kiel, 2009 (160 pages) (English abstract included).

*Primary Examiner* — Timothy R Rozof
(74) *Attorney, Agent, or Firm* — Clark & Elbing LLP; Kristina Bicker-Brady (57) ABSTRACT

New phenanthroline derivatives as drug as well as methods for producing said compounds are provided.

11 Claims, 8 Drawing Sheets

PYRIDO [3,4-C] [1,9] PHENANTHROLINE AND 11, 12 DIHYDROPYRIDO [3,4-C] [1,9] PHENANTHROLINE DERIVATIVES AND THE USE THEREOF, PARTICULARLY FOR TREATING CANCER

The present invention relates to novel aromatic heterocycles, a process for their preparation as well as medicaments containing these heterocycles.

Many cancer diseases are not treatable by selectively acting active agents so far. According to the World Health Organization (WHO) about 10 million people were diagnosed with cancer worldwide in 2000, ca. 6 million died (World Cancer Report 2003, www.iarc.fr/IARCPress/pdfs/wcr/WorldCancerReport.pdf). Based on the estimation of the WHO, the number of deaths caused by cancer diseases will increase until 2030 to ca. 11.5 million per year (Worlds Health Statistics—2007, www.who.int/whosis/whostat2007_10-highlights.pdf). In view of the large number of people who have cancer, the unfavorable prognosis for curing certain cancer types due to poor efficacy of existing medicaments, side effects and development of resistance to used medicaments, there is an urgent need for new cancer medicaments.

6-aminobenzo[c]phenanthridines are known from DE 195 38 088 A1, that partly have antitumor, antimicrobial, antifungal, antiviral and anti-inflammatory properties. Said compounds have yet disadvantages in the pharmacological profile, in particular in low water solubility.

It is therefore an object of the invention to provide novel medicaments. Furthermore, it is an object of the invention to provide novel medicaments in particular for therapy against cancer diseases. A further object of the invention is to provide novel medicaments with a pharmaceutically acceptable water solubility as well as a manufacturing method as described below, through which the compounds according to the present invention can be obtained.

The object is solved by embodiments indicated in the claims and present description. The dependent claims and examples specify advantageous embodiments of the invention.

In one aspect the present invention relates to the provision of phenanthroline derivatives of the general formulas I and II

I

II wherein $R^1$ is equal to a phenyl ring of the formula which carries at least one substituent $R^X$ selected from the group Cl, Br or I in the meta position, wherein $R^Y$, which may be identical or different, is equal to H, OH, OMe, OEt or halogen; as well as of the general formulas III and IV,

III

IV wherein $R^1$ is either equal to a phenyl ring of the formula which carries at least one substituent $R^Y$ in the meta position, wherein $R^Y$, which may be identical or different, is equal to H, OH, OMe, OEt or halogen or is equal to a five-membered aromatic heterocycle of the formula wherein W is equal to O, S or NH; and
wherein Z is equal to H, F, Cl, Br, I, NHX, OX, SX, wherein X is equal to an H, dimethylaminoalkyl, diethylaminoalkyl, ω-(1,3-diazol-1-yl)-alkyl-, hydroxyalkyl, alkoxyalkyl, thiolalkyl, alkylthioalkylgroup,
wherein alkyl is equal to methyl, ethyl or propyl
and wherein A is equal to O or S,
as well as the pharmaceutically acceptable salts, solvates and prodrugs thereof.

In a further aspect, the invention relates to a process for preparing a compound according to the present invention as described above comprising at least the following steps:
(i) conversion of substituted aldehydes of general formula $R^1$—CHO (V) with substituted 4-methylpyridine-3-carbonitriles of the general formula

VI in aprotic bipolar solvents in the presence of bases to a compound of the general formula

VII (ii) isolation of the products and derivatization at position 6 with insertion of the residues $R^4$ to the derivatives with A or Z substitution at position 6 according to formula I to IV wherein $R^1$ is an H, a cyclic or acyclic, branched or unbranched aliphatic hydrocarbon residue, singly or multiply substituted, an aromatic carbocyclic or heterocyclic residue, singly or multiply substituted, and $R^2$ and $R^3$ may be identical or different and is H, alkyloxy residue, alkyleneoxy residue, a halogen atom or a nitro group, and $R^4$ is an H, a monoamino, alkylamino, dialkylamino, (dialkyl)aminoalkylamin, alkyl, alkoxy, (dialkyl)aminoalkyloxy, hydroxy, hydroxyalkylamino, hydroxyalkyloxy, thiol, (dialkyl)aminoalkylthio, thioalkyl, alkylthioalkyl group or a halogen atom.

The subsequent derivatization at position 6 with insertion of the $R^4$ residues to the derivatives with A or Z substitution at position 6 corresponding to method step (ii) leads to the compounds according to the present invention as shown in the general formula III or IV.

Therefore, the present invention relates to a process for preparing a compound as described above, wherein between the two steps (i) and (ii) optionally the method step
(i.a.) dehydration and isolation of the resulting products of the general formula

VIII can be introduced.

Particularly, the present invention relates to a method as described above, wherein the aprotic dipolar solvent is preferably an amide such as dimethylformamide, dimethylacetamide, diethylacetamide, hexamethylphosphoracidtrisamide or a urea such as tetramethylurea, 1,3-dimethyltetrahydropyrimidine-2-one and 1,3-dimethylimidazolidinone or a dimethylsulfoxide and wherein the base is an alkali or alkaline earth hydride such as sodium hydride, alkali amide such as sodium amide, sodiummethylacetamide, alkali, alkaline earth or aluminum alcoholate such as potassium tert-butylate, sodium methylate, sodium ethylate or aluminum ethylate.

It has been shown in the experiments carried out according to the present invention that it is surprisingly possible to obtain the phenanthroline derivatives according to the present invention through simple conversion of correspondingly substituted aldehydes with correspondingly substituted 4-methylpyridine-3-carbonitriles.

The reaction procedure can be represented as follows:

In detail, the approach is such that a conversion of an aldehyde of the formula $R_1$—CHO  V, wherein $R^1$ may be a hydrogen, a cyclic or acyclic, branched or unbranched aliphatic hydrocarbon residue, which can be singly or multiply substituted, as well as an aromatic carbocyclic or heterocyclic residue, which may be singly or multiply substituted, with 2 moles of a 4-methylpyridine-3-carbonitrile of the formula VI,

VI wherein $R^2$ and $R^3$, which may be identical or different, stand for an H, an alkyloxy residue, an alkylenoxy residue, a halogen atom or a nitro group, occurs in the presence of base in an aprotic dipolar solvent to a 6-amino-11,12-dihydropyrido[3,4-c][1,9]phenanthroline of formula VII.

After isolation by precipitation of the free base, filtration and subsequent purification, for example recrystallization (*Organikum*, 21$^{st}$ edition, 2001, Wiley-VCH), these derivatives of formula VII may be converted with corresponding chemical methods (diazotization, conversion of carboxylic acid derivatives with inorganic acid chlorides, nucleophilic aromatic substitution, synthesis of thiones/thiols and reduction reactions, such as e.g. desulphurizations) for the corresponding residues $R^4$ at position 6, which are known by the person skilled in the art, for example from *Organikum*, 21$^{st}$ edition, 2001, Wiley-VCH or *Organic Chemistry*, K. Peter C. Vollhardt, 3$^{rd}$ edition, 2000, in one or more steps to the derivatives of formula I or II or it may occur a dehydrogenation according to commonly known methods to the skilled person (e.g. of "Comprehensive Organic Transformations", Richard C. Larock, 1989) with a suitable dehydrogenating agent in absence or presence of a solvent to the corresponding 6-aminopyrido[3,4-c][1,9]phenanthrolines of the formula VIII, which subsequently after isolation may be converted with known chemical methods by the skilled person (*Organikum*, 21$^{st}$ edition, 2001, Wiley-VCH; *Organic Chemistry*, K. Peter C. Vollhardt, 3$^{rd}$ edition, 2000) for the corresponding residues for $R^4$ at position 6, in one or more steps to the derivatives of formula III or IV, wherein $R^4$ may be a hydrogen atom, a monoaminogroup, an alkylamino group, a dialkylamino group, a (dialkyl)aminoalkylaminogroup, an alkyl group, an alkoxy group, a (dialkyl)aminoalkyloxygroup, a hydroxy group, a hydroxyalkylamino group, a hydroxyalkyloxy group, a thiol group, a (dialkyl)aminoalkylthiogroup, a thioalkylaminogroup, a thiolalkylthiogroup as well as a halogen atom. A selection of N-substituted alkylene diamine side chains at position 6 is e.g. shown by Genès (Genès et al., Eu. J. Med. Chem. (46), 2011, 2117-2131). The import of oxygen, sulfur and carbon nucleophiles is as described by e.g. Cherng (Cherng, Tetrahedron 58, 2002, 4931-4935), furthermore, the generally applicable methods of nucleophilic substitution at aromatic compounds, known by the person skilled in the art of *Organikum*, 21$^{st}$ edition, 2001, Wiley-VCH or *Organic Chemistry*, K. Peter C. Vollhardt, 3$^{rd}$ edition, 2000.

As aprotic dipolar solvents for the reaction according to the present invention for the preparation of correspondingly substituted 6-amino-11,12-dihydropyrido[3,4-c][1,9]phenanthrolines of formula VII preferably amides such as dimethylformamide, dimethylacetamide, diethylacetamide, hexamethylphosphoracidtrismide or urea such as tetramethyl urea, 1,3-dimethyltetrahydro-pyrimidine-2-one and 1,3-dimethylimidazolidinone or dimethylsulfoxide can be used.

As base the following can be used for example:

Alkali or alkaline earth hydrides such as sodium hydride, alkali amides such as sodium amide, sodium methylacetamide, alkali, alkaline earth or aluminum alcoholates, such as potassium tert.-butylate, sodium methylate, sodium ethylate or aluminum ethylate.

The reaction may be carried out as follows: To a solution of the base in a suitable dipolar solvent, a solution of the compound V and VI in the same solvent is slowly added dropwise under inert gas. After several hours of stirring at 25-40° C. under inert gas, the mixture is poured on ice water and the residue is filtered off. The filtered solution is shaken out with a suitable organic solvent. The organic phase is to a large extent concentrated and thereafter distilled in vacuo. The combined residues may be purified by recrystallization in a suitable solvent. The 6-amino-11,12-dihydropyrido[3,4-c][1,9]-phenanthroline VII may then be dehydrated according to generally applicable methods (Comprehensive Organic Transformations, Richard C. Larock, 1989) with a suitable dehydrogenating agent in the presence or absence of an inert solvent to 6-amino-pyrido[3,4-c][1,9]phenanthroline VIII. The amino group in position 6 may be replaced in one or more steps with generally applicable chemical methods (e.g. *Organikum*, 21$^{st}$ edition, 2001, Wiley-VCH; *Organic Chemistry*, K. Peter C. Vollhardt, 3$^{rd}$ edition, 2000) with the above-mentioned residues $R^4$, so that one arrives at the formulas I or II, or for the 11,12-dehydrogenated derivatives at the formulas III or IV, respectively.

Of particular note in the process according to the present invention is that it allows to synthesize phenanthroline derivatives, which have in position 11, both, aliphatic as well as substituted or unsubstituted aromatic residues. It is surprising that the synthesis with the above-described simple reaction is possible, wherein due to the aldehyde starting material to be used a very large range of variation exists in relation to the products to be obtained. In addition, at the position 6 a considerable variability is obtained due to the possibility of replacing the amino group against the mentioned residues. Based on the combination of the both variable positions a very large range of compounds and the possibility of building a large library of potentially cytostatically effective substances is resulted.

In one aspect, the present invention also relates to compounds, which are obtainable by a process as described above.

In a further aspect the invention relates to the above compounds for use as a medicament, in particular for the use in cancer therapy.

A compound according to the present invention as described above is preferred for use in the treatment of a disease selected from the group consisting of microbial, fungicidal, viral and/or inflammatory diseases.

Furthermore, the invention also relates in one aspect to the compound according to the present invention as described above, for use in the treatment of cancer.

Preferably, the cancer is selected from the group consisting of leukemia, melanoma or mamma carcinoma.

Furthermore, the present invention relates to a pharmaceutical composition comprising at least one of the compound described above in combination with a suitable excipient.

It has been shown in the experiments carried out according to the present invention that the above-described phenanthroline derivates have antitumoral properties. Due to their structural similarity it is to be assumed that they have also antimicrobial, antifungal, antiviral and anti-inflammatory properties like the benzo[c]phenanthridines. For investigating the pharmacological properties the compounds of general formulas I and II, as well as compounds of the substance class III were investigated in an "in vitro anti-tumor screening" of the National Cancer Institute (NCI), Bethesda, Md., USA. 60 different human pathogenic tumor cell lines were tested, which originate from nine cancer types (leukemia, non-small cell lung carcinoma, colon cancer, CNS cancer, melanoma, ovarian cancer, renal cancer, prostate cancer, breast cancer). For determining the efficacy, the tumor cells are exposed to the compounds for two days and thereafter the growth inhibition is indirectly determined through the determination of the protein biomass with sulforhodamine B (SRB). Untreated cultures serve as reference.

$R^4 = A, Z$

Structural formula of the tested compounds of the phenanthroline derivatives of the formulas I and II according to the present invention at the National Cancer Institute (NCI).

In the analyses according to the present invention, the derivatives were initially tested at a concentration of 1 µM to the 60 cell lines. Growth inhibitions could be observed for several derivatives. Surprisingly, the compounds according to the present invention showed activities, which are outside of the category of anti-tumor compounds, which were examined similarly, so that a whole new efficient spectrum is obtained.

Table I shows the results of this test, selected for 7 different derivatives of the phenanthroline derivatives according to the present invention of the formulas I and II having different residues in position 11 and the position 6. The respective residues are shown in the first two rows. The left column shows the cell lines used from 3 selected tumor types, leukemia, melanoma, as well as breast cancer. The table makes statements about growth inhibitory effects of the corresponding derivatives with their different residues.

TABLE I

Cytotoxicity tests of 60 tumor cell lines (c = 1 μM) with derivatives of formulas I and II by the NCI.

| | Residue in position 11 | | | |
|---|---|---|---|---|
| |  |  |  |  |
| Residue in position 6 | NH₂ | OH | NH₂ | NH₂ |
| Cell lines | Percentage cell growth | | | |
| Leukemia | | | | |
| CCRF-CEM | 5.9 | 37.1 | — | — |
| HL-60(TB) | −11.6 | −16.1 | 3.1 | 76 |
| MOLT-4 | 0.5 | 24.6 | 14.2 | 89.4 |
| RPMI-8226 | 6.3 | 52.6 | — | — |
| SR | 0.4 | 10.6 | 3 | 91.8 |
| K-562 | — | — | 14.9 | 99.7 |
| Arithmetic mean | 0.3 | 21.8 | 8.8 | 89.2 |
| Melanoma | | | | |
| LOX IMVI | 38 | 44.6 | 44.2 | 89.7 |
| MALME-3M | — | 50 | 43.9 | 108.6 |
| M14 | 1.3 | 29.3 | 34.5 | 108.4 |
| MDA-MB-435 | −59.8 | 1.1 | −39 | 117.6 |
| SK-MEL-2 | 29.9 | 46.4 | −10.5 | 101.4 |
| SK-MEL-28 | 73.6 | 52.1 | 60.6 | 117 |
| SK-MEL-5 | 17.2 | 28 | −52.2 | 101.1 |
| UACC-257 | 48.7 | 88.5 | 66 | 106 |
| UACC-62 | 50.3 | 26.4 | 41.4 | 96.8 |
| Arithmetic mean | 24.9 | 40.7 | 14.3 | 105.2 |
| Breast cancer | | | | |
| MCF7 | 27.8 | 25.3 | 19.5 | 91.2 |
| MDA-MB-231/ATCC | 68.2 | 52.7 | 63 | 106 |
| HS-578T | 20.3 | 51.3 | −0.7 | — |
| BT-549 | 29.7 | 53.5 | 44.7 | 103.5 |
| T-47D | 75.5 | 60.3 | 57.4 | 98.9 |
| MDA-MB-468 | −4.5 | 21 | −22.3 | 103.3 |
| Arithmetic mean | 36.2 | 44 | 30.3 | 100.6 |
| Arithmetic mean of all 60 cell lines | 34.1 | 33.4 | 46.1 | 102.1 |

| | Residue in position 11 | | |
|---|---|---|---|
| |  |  |  |
| Residue in position 6 | NH₂ | NH₂ | NH₂ |
| Cell lines | Percentage cell growth | | |
| Leukemia | | | |
| CCRF-CEM | — | 76.5 | — |
| HL-60(TB) | 70.3 | 78.8 | 102.7 |
| MOLT-4 | 75.3 | 85.9 | 86.2 |
| RPMI-8226 | 64.7 | 92.3 | — |
| SR | — | 41.4 | 75.5 |
| K-562 | 84.9 | — | 87.6 |
| Arithmetic mean | 73.8 | 75 | 70.4 |

TABLE I-continued

Cytotoxicity tests of 60 tumor cell lines (c = 1 μM) with derivatives of formulas I and II by the NCI.

| Melanoma | | | |
|---|---|---|---|
| LOX IMVI | 95.7 | 86.3 | 107.3 |
| MALME-3M | 98.2 | 93.1 | 115.4 |
| M14 | 93.4 | 105.8 | 120.5 |
| MDA-MB-435 | 107 | 17.2 | 99.3 |
| SK-MEL-2 | 94.1 | 117.2 | 133.1 |
| SK-MEL-28 | 112.5 | 100.45 | 115.3 |
| SK-MEL-5 | 86.2 | 85.05 | 95.8 |
| UACC-257 | 107.8 | 110.9 | 110 |
| UACC-62 | 81.7 | 95.5 | 104.1 |
| Arithmetic mean | 97.4 | 90.2 | 100.1 |
| Breast cancer | | | |
| MCF7 | 83.4 | 81.6 | 88.6 |
| MDA-MB-231/ATCC | 80.6 | 91.5 | 106.9 |
| HS-578T | — | 82.3 | 111.1 |
| BT-549 | 67.8 | 91.6 | 144.3 |
| T-47D | 84.6 | 104.9 | 111.8 |
| MDA-MB-468 | 87.6 | 48.9 | 104.5 |
| Arithmetic mean | 80.8 | 83.5 | 111.2 |
| Arithmetic mean of all 60 cell lines | 90.5 | 109 | 106.5 |

The first three derivatives show significant growth inhibitions on the cells of tumor types selected for the example, while the remaining four derivatives have no, to very little growth inhibitory effects on these cells. This implies that a 3-halophenyl residue in position 11 is essential for the growth inhibitory effect of phenanthroline derivatives of formulas I and II. Neither derivatives having halogen atoms in the position 2 or 4 (in the example 2-bromophenyl, or 4-bromophenyl, respectively) nor derivatives with other functional groups in position 3 of the phenyl ring, nor the unsubstituted phenyl ring shows growth inhibitory effects in this extent. Table II shows the results of this test, selected for 5 different derivatives of phenanthroline derivatives of the formula III according to the present invention having different residues in position 11. The residues in position 11 are shown in the first row. The left column shows the used cell lines from 3 selected tumor types, leukemia, melanoma, as well as breast cancer.

The table makes statements about growth inhibitory effects of the corresponding derivatives with their different residues.

Structural formula of the tested compounds of the phenanthroline derivatives according to the present invention of formula III at the National Cancer Institute (NCI).

TABLE II

Cytotoxicity tests of 60 tumor cell lines (c = 1 μM) with derivatives of formula III by NCI.

| | Residue in position 11 | | | | |
|---|---|---|---|---|---|
| | phenyl | 3-OMe phenyl | 2,3-diOMe phenyl | 2,4,6-triOMe phenyl | furyl |
| Cell lines | Percentage cell growth | | | | |
| Leukemia | | | | | |
| CCRF-CEM | 21.7 | 32.1 | 74.9 | 7.2 | 12.4 |
| HL-60(TB) | 18.9 | 26.0 | 118.7 | −0.9 | 13.9 |
| MOLT-4 | 2.3 | 11.9 | 90.1 | −8.9 | −0.9 |
| RPMI-8226 | 80.7 | 76.2 | 96.8 | 33.5 | 62.7 |
| SR | 11.1 | 15.3 | 83.5 | 13.1 | 7.8 |
| K-562 | 80.0 | 68.9 | 88.8 | 29.9 | 51.6 |
| Arithmetic mean | 35.8 | 38.4 | 92.1 | 12.3 | 24.6 |
| Melanoma | | | | | |
| LOX IMVI | 41.0 | 37.9 | 89.3 | −30.4 | 2.3 |
| MALME-3M | 91.0 | 73.7 | 123.8 | 35.5 | 59.7 |
| M14 | 74.7 | 59.1 | 94.8 | 9.5 | 37.0 |

TABLE II-continued

Cytotoxicity tests of 60 tumor cell lines (c = 1 µM) with derivatives of formula III by NCI.

Residue in position 11

| | OMe (phenyl) | OMe (meta) | OMe, OMe (2,3) | MeO, OMe, MeO | OMe (furyl) |
|---|---|---|---|---|---|
| MDA-MB-435 | — | — | — | — | — |
| SK-MEL-2 | 141.3 | 103.9 | 117.3 | 65.3 | 91.8 |
| SK-MEL-28 | 102.1 | 69.4 | 119.5 | 41.5 | 42.4 |
| SK-MEL-5 | 64 | 51.2 | 86.3 | 2.2 | 20.0 |
| UACC-257 | 124.5 | 78.0 | 126.3 | 30.9 | 69.8 |
| UACC-62 | 79.3 | 45.2 | 99.1 | — | 41.0 |
| Arithmetic mean | 89.9 | 64.8 | 95.2 | 22.1 | 45.5 |
| Breast cancer | | | | | |
| MCF7 | 39.8 | 37.1 | 89.9 | 22.8 | 25.0 |
| MDA-MB-231/ATCC | 112.0 | 77.1 | 90.8 | — | 74.9 |
| HS-578T | 83.9 | 64.2 | 90.5 | -2.5 | — |
| BT-549 | 59.4 | 61.4 | 95.0 | 8.31 | 16.2 |
| T-47D | 97.0 | 77.7 | 97.4 | 36 | 48.4 |
| MDA-MB-468 | 98.2 | 53.7 | 81.5 | -23.6 | 35.6 |
| Arithmetic mean | 81.7 | 61.9 | 90.9 | 8.2 | 40.0 |
| Arithmetic mean of all 60 cell lines | 69.9 | 55.6 | 98.0 | 16.8 | 39.1 |

Table II shows the best results in terms of a growth inhibiting effect for the derivative with a trimethoxyphenyl residue in position 11. The derivative with only one methoxy group in the meta position also achieves significant growth inhibitions. The 11-phenyl derivative has only a small effect, while a substitution in o-position proves to be disadvantageous in the example of 2,3-dimethoxyphenyl derivative. This implies that a substituent must be present at least in the meta position of the 11-phenyl ring. In light of the results of Table I, it is to be expected that the replacement of methoxy by halogen in meta position likewise leads to good growth inhibitory effects. As a representative of a five-membered heteroaromate, the 11-furyl derivative shows here good cytotoxic effects.

Furthermore, it can be seen from tables I and II that the here tested phenanthrolin derivatives according to the present invention have selectivities for certain tumor types. The most marked growth inhibitory effect is for tumor cells of leukemia. Furthermore, a degree of selectivity for tumor cells of melanoma and mamma carcinoma (breast cancer) can be seen. These results are representative for all 60 cell lines. Of the most potent compounds further dose-response relationships were determined for 5 concentrations. The $GI_{50}$ (growth inhibition 50%) describes here the concentration of the test substance required for inhibiting cell growth by 50%. Hence the so-called "mean-graph midpoint" (MG_MID) is determined which corresponds the mean of the logarithms $GI_{50}$ values of an average response of all 60 cell lines for the test substance examined [Boyd and Paull, *Drug. Develop. Res.*, 34, (1995) 91-109,]

$$MG_{MID} = \frac{\sum \log GI_{50}}{60}$$

This size allows to characterize the activity of a compound in the used test system and to compare quantitatively with the activity of other compounds (table 3). The following table shows 4 derivatives of the formulas I and III with their used codes, for the respective substances determined mean graph midpoints and the therefrom calculated $GI_{50}$ values.

| Code | MG_MID | $\sum \frac{GI_{sc}}{60}$ [µM] |
|---|---|---|
| P4 | -5.09 | 8.13 |
| P5 | -5.57 | 2.69 |
| P5-O | -5.07 | 8.51 |
| P16 | -5.42 | 3.80 |
| P26 | -5.22 | 6.02 |
| Fagaronine | -5.00 | 9.48 |

Legend to Table 3:
P4=6-amino-11,12-dihydropyrido[3,4-c][1,9]phenanthroline, P5=6-amino-11-(3-bromophenyl)-11,12-dihydropyrido-[3,4-c][1,9]phenanthroline, P5-O=11-(3-bromophenyl)-6-oxo-5,6,11,12-tetrahydropyrido[3,4-c][1,9]phenanthroline, P16=6-amino-11-(3-chlorophenyl)-11,12 dihydropyrido-[3,4-c][1,9]phenanthroline, P26=6-amino-11-(3,4-di-chlorophenyl)-11,12-dihydropyrido-[3,4-c][1,9] phenanthroline.

In addition to the compounds according to the present invention, fagaronine was tested, which is a herbal benzo[c]phenanthridine alkaloid, which is considered as the lead compound for the development of synthetic benzo[c]phenanthridine derivatives (Pommier, Y. Nat. Rev. Cancer, 6, (2006), 789; Pommier, Y. Chem. Rev. 109, (2009), 2984). It should be noted that all derivatives of the phenathroline according to the present invention for which dose-response curves have been determined, show a better growth inhibiting effect, than the natural product fagaronine.

Exemplary for 6-amino-11-(3-bromophenyl)-11,12-dihydropyrido[3,4-c][1,9]phenanthroline are the dose-response curves shown in FIGS. 1 to 9. The nine different Figures include the various types of cancer. The percentage of growth, depending on the concentration of the compound is plotted (as log₁₀ of the molar concentrations). The individual curves for each type of cancer are different cell lines of this type of cancer, which appear as legends in their usual abbreviations. Horizontal lines in the Figures denote percent growth +100, +50, 0, −50, −100. 100% growth means e.g. no difference to growth after two days without added substance. It can be seen in each curve that with increasing concentrations of the substance, the percent growth decreases.

Figure 1:
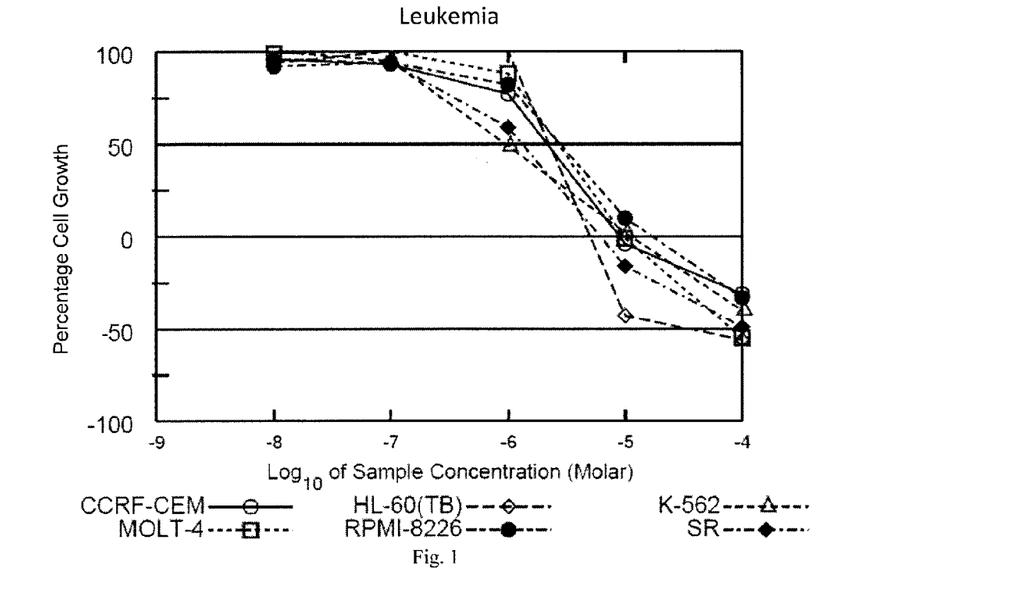
FIG. 1: Dose response curves for leukemia tumors from the 5 dose assay (NCI) for 6-amino-11-(3-bromophenyl)-11,12-dihydropyrido[3,4-c][1,9]phenanthroline
Figure 2:
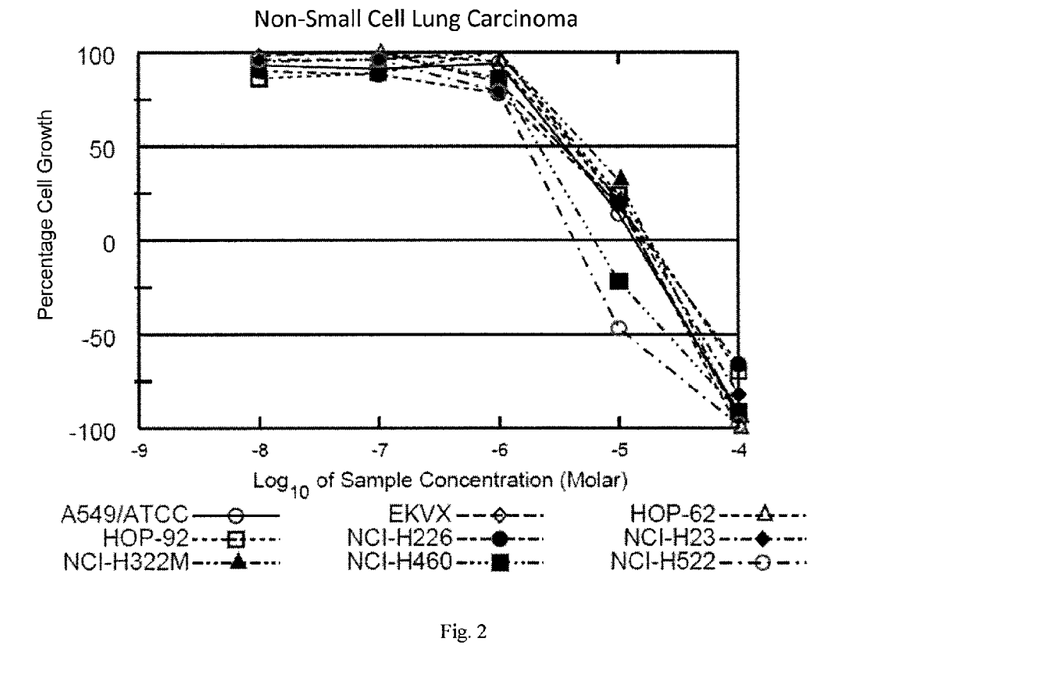
FIG. 2: Dose response curves for non-small cell lung cancer from the 5 dose assay (NCI) for 6-amino-11-(3-bromophenyl)-11,12-dihydropyrido[3,4-c][1,9]phenanthroline
Figure 3:
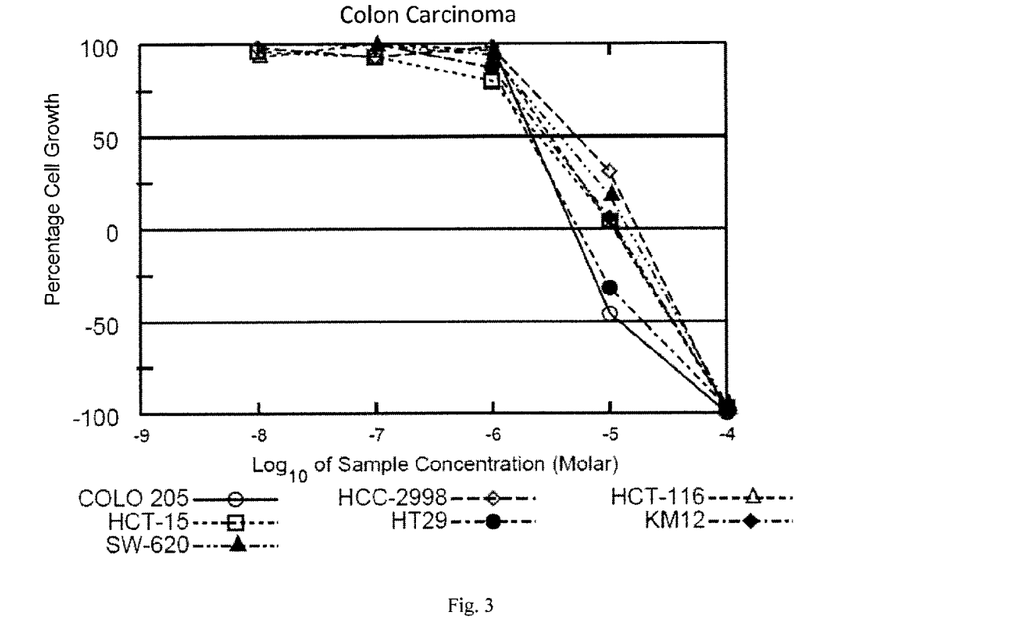
FIG. 3: Dose response curves for colon carcinomas from the 5-dose-assay (NCI) for 6-amino-11-(3-bromophenyl)-11,12-dihydropyrido[3,4-c][1,9]phenanthroline
Figure 4:
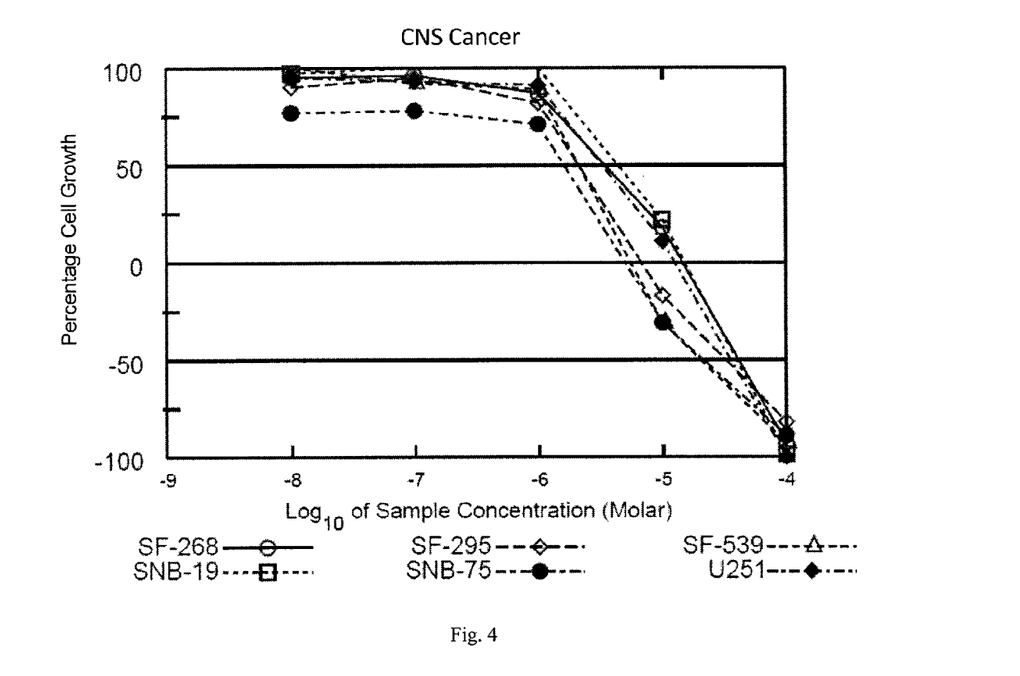
FIG. 4: Dose response curves for CNS cancer from the 5 dose assay (NCI) for 6-amino-11-(3-bromophenyl)-11,12-dihydropyrido[3,4-c][1,9]phenanthroline
Figure 5:
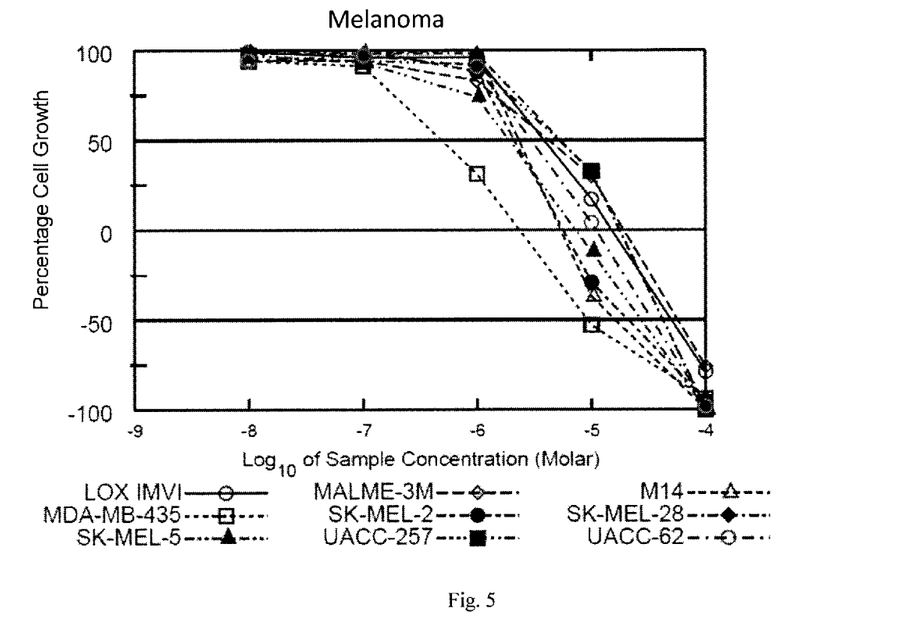
FIG. 5: Dose response curves for melanomas from the 5 dose assay (NCI) for 6-amino-11-(3-bromophenyl)-11,12-dihydropyrido[3,4-c][1,9]phenanthroline
Figure 6:
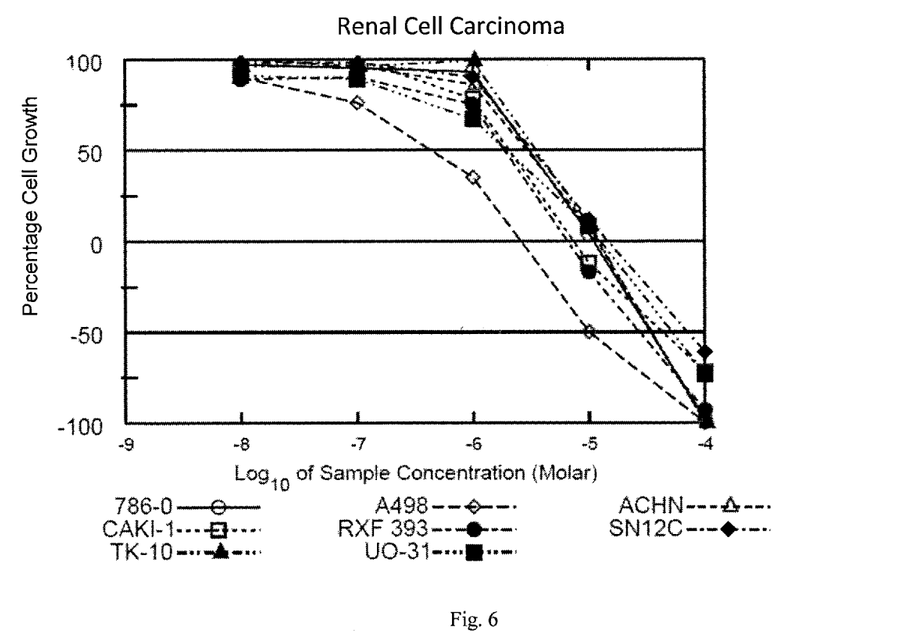
FIG. 6: Dose response curves for renal cell carcinomas from the 5 dose assay (NCI) for 6-amino-11-(3-bromophenyl)-11,12-dihydropyrido[3,4-c][1,9]phenanthroline
Figure 7:
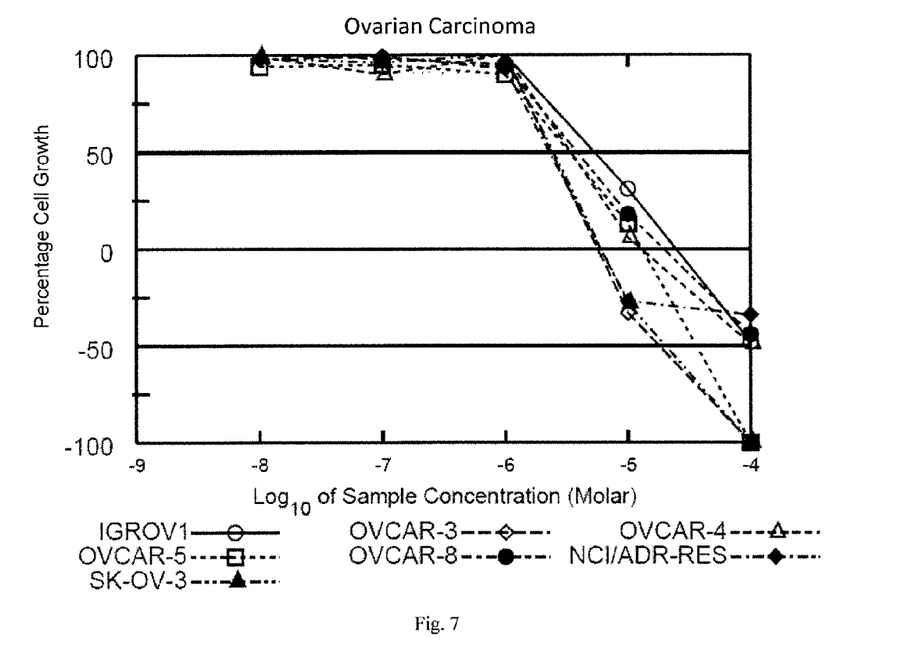
FIG. 7: Dose response curves for ovarian carcinomas from the 5 dose assay (NCI) for 6-amino-11-(3-bromophenyl)-11,12-dihydropyrido[3,4-c][1,9]phenanthroline
Figure 8:
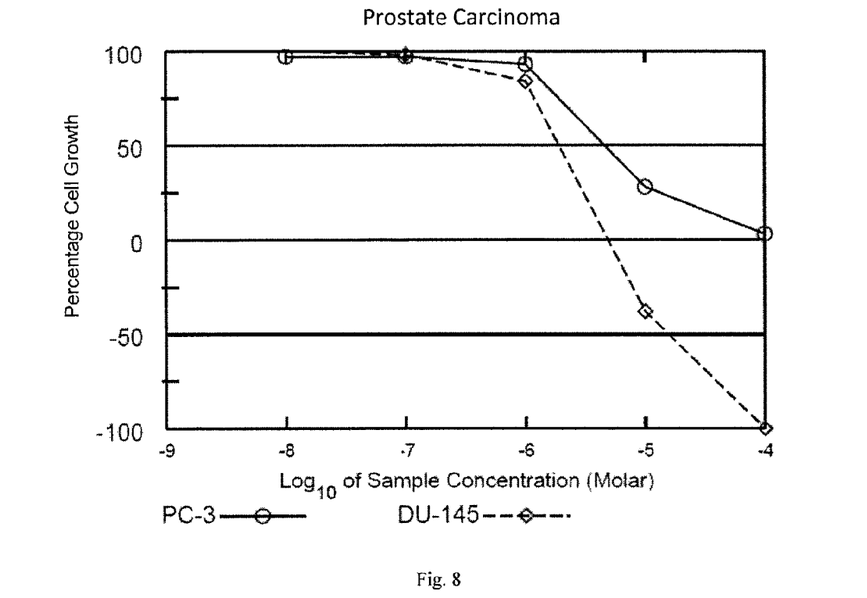
FIG. 8: Dose response curves for prostate carcinomas from the 5 dose assay (NCI) for 6-amino-11-(3-bromophenyl)-11,12-dihydropyrido[3,4-c][1,9]phenanthroline
Figure 9:
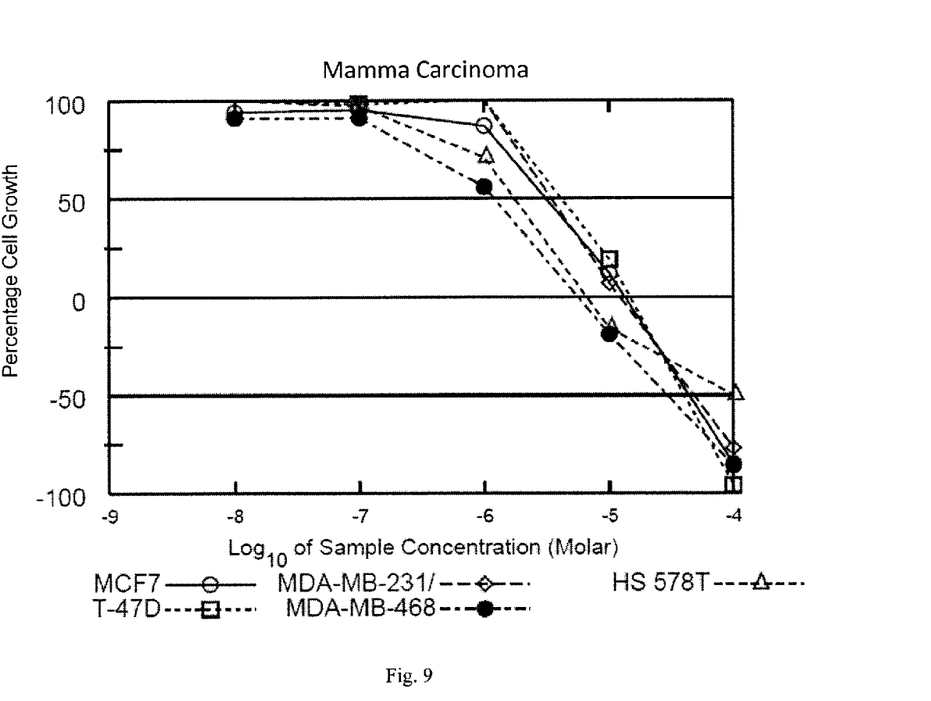
FIG. 9: Dose-response curves for mamma carcinomas from the 5 dose assay (NCI) for 6-amino-11-(3-bromophenyl)-11,12-dihydropyrido[3,4-c][1,9]phenanthroline
Figure 10:
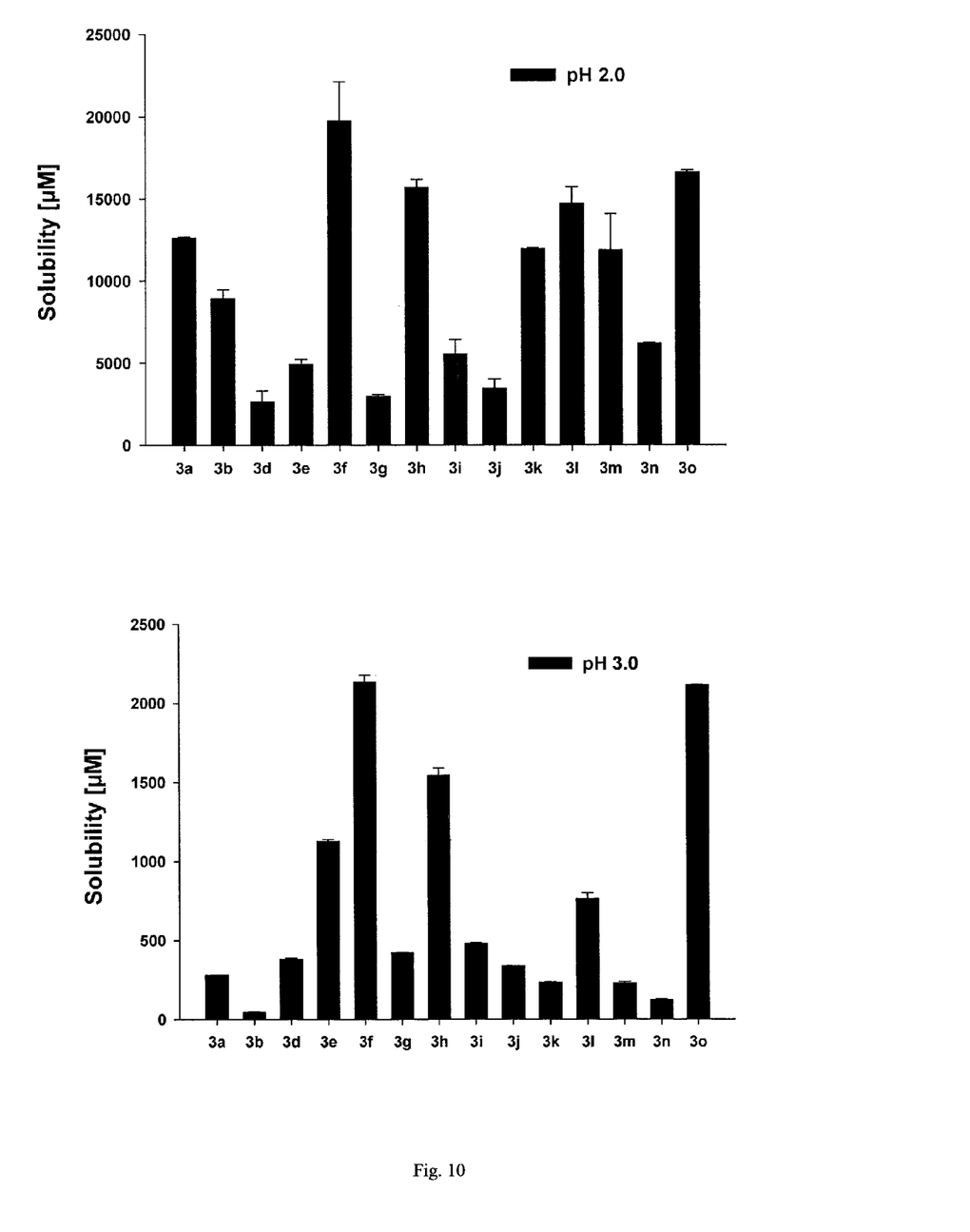
FIG. 10: pH-dependent solubilities of 6-amino-11-(3-bromophenyl)-11,12-dihydropyrido[3,4-c][1,9]phenanthroline

A particular advantage of phenanthroline derivatives according to the present invention is their improved water solubility as compared to the 6-aminobenzo[c]phenanthridines. In particular, the solubility in acidic aqueous media to give (2-20 mM in phosphate buffer of pH=2, and 0.01 or 0.5 mmol in a phosphate buffer pH=4) is to be noted hereby, which is due to two additional protonatable nitrogen atoms. At pH 7.4 solubilities of many derivatives were found in the low micromolar range (<1-15 µM), the solubility of 6-aminobenzo[c]phenanthridine at this pH is predominantly in the nanomolar range. FIG. 10 shows 4 individual graphics, standing for 4 phosphate buffer systems with different pH values, in which the solubility of the novel 6-amino-11,12-dihydropyrido-[3,4-c][1,9]phenanthroline according to the present invention are plotted on the y-axis, while on the x-axis, the various derivatives having different residues in position 11 (3a: R=phenyl, 3b: R=3-methoxyphenyl, 3d: R=2,3-dimethoxyphenyl, 3e: R=3,5-dimethoxyphenyl, 3f: R=3,4,5-trimethoxyphenyl, 3g: R=2,4,6-trimethoxyphenyl, 3h: R=furyl, 3i: R=thienyl, 3j: R=3-bromophenyl, 3k: R=4-bromophenyl, 3l: R=3-chlorophenyl, 3m: R=4-fluorophenyl, 3n: R=biphenyl, 3o: R=propyl) can be seen.

Figure 11:
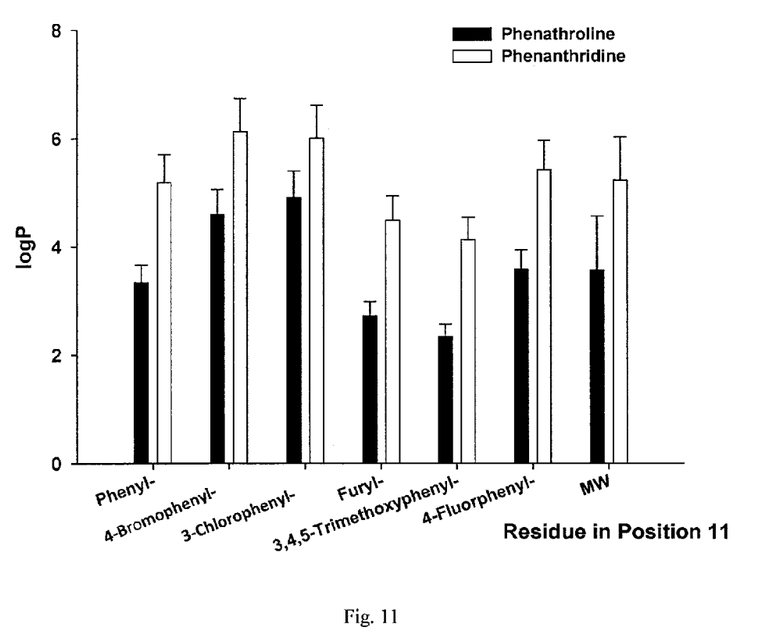
FIG. 11: log P values depending on the residua in position 11

In addition, log P values of the phenanthroline derivates according to the present invention were determined as a measure of the lipophilicity of the substance class. Six different 6-amino-11,12-dihydropyrido[3,4-c][1,9]phenanthroline with different residues in position 11 were compared thereby with the corresponding benzo[c]phenanthridines. FIG. 11 shows the log P values on the y-axis versus the derivatives that differ in the six designated residues in position 11, respectively, for the two compared substance classes. Furthermore, the mean (MW) is denoted.

From the graph it can be seen that the log P values of the 6-amino-11,12-dihydropyrido[3,4-c][1,9]phenanthrolines according to the present invention are lower than average of about the value 2 of the corresponding benzo[c]phenanthridines.

This is of tremendous importance, considering the suitability of the substance class as a medicament and particularly its oral bioavailability. According to the "Rule of Five" of Lipinski (Lipinski, C. A.; Lombardo, F.; Dominy, B. W.; Feeney, P. J. *Adv. Drug. Deliv. Rev.* 46 (2001), 3-26), a generally accepted rule of thumb for estimation of oral bioavailability of a potential medicament, a substance is orally bioavailable, if it does not have more than five donors of hydrogen bonds (e.g. OH or NH groups), not more than ten acceptors of hydrogen bonds (e.g. oxygen or nitrogen atoms), a molecular weight of not more than 500 g/mol, as well as a partition coefficient (log P) between octanol and water (octanol water partition coefficient) of a maximum of 5. The investigated derivatives according to the present invention all lie within the thresholds of the "Rule of Five" and are thereafter as orally applicable medicaments, e.g. in the form of solutions, tablets, capsules, etc.

The drawings show dose-response curves of 9 different tumor types from the 5 dose assay (NCI) for 6-amino-1'-(3-bromophenyl)-11,12-dihydropyrido[3,4-c][1,9]phenanthroline.

BRIEF DESCRIPTION OF THE DRAWINGS

The invention claimed is:
1. A compound
(i) of general formula I or II

I

II wherein $R^1$ is equal to a phenyl ring of the formula $R^X$ is selected from Cl, Br or I, and each $R^Y$ is, independently, selected from H, OH, OMe, OEt or halogen; or

(ii) a compound of the general formula III or IV, wherein $R^1$ is either equal to a phenyl ring of the formula which carries at least one substituent $R^Y$ in the meta position, wherein each $R^Y$ is, independently, selected from H, OH, OMe, OEt, halogen, or is equal to a five-membered aromatic heterocycle of the formula wherein
W is selected from O, S, or NH;
Z is selected from H, F, Cl, Br, I, NHX, OX, and SX;
X is selected from H, dimethylaminoalkyl, diethylaminoalkyl ω-(1,3-diazol-1-yl)-alkyl, hydroxyalkyl, alkoxyalkyl, thiolalkyl, alkylthioalkyl group, wherein alkyl is equal to methyl, ethyl or propyl; and
A is equal to O or S,
and pharmaceutically acceptable salts, solvates and prodrugs thereof.

2. A process for preparing a compound according to claim 1, comprising:

(i) reacting a substituted aldehyde of general formula $R^1$—CHO (V) with a substituted 4-methylpyridine-3-carbonitrile of the general formula in aprotic bipolar solvents in the presence of base to form a compound of the general formula and (ii) derivatization of the $NH_2$ moiety at position 6 with residues $R^4$ and/or conversion to the derivatives with A or Z substitution at position 6, according to formula I to IV, wherein
$R^1$ is an H, a cyclic or acyclic, branched or unbranched aliphatic hydrocarbon residue, singly or multiply substituted, an aromatic carbocyclic or heterocyclic residue, singly or multiply substituted, and each of $R^2$ and $R^3$ is, independently, selected from H, alkyloxy residue, alkylenoxy residue, a halogen atom or a nitro group, and
$R^4$ is an H, a monoamino, alkylamino, dialkylamino, (dialkyl)aminoalkylamin, alkyl, alkoxy, (dialkyl)aminoalkyloxy, hydroxy, hydroxyalkylamino, hydroxyalkyloxy, thiol, (dialkyl)aminoalkylthio, thioalkyl, alkylthioalkyl group or a halogen atom.

3. A method according to claim 2, further comprising, between the two steps (i) and (ii),
dehydration and isolation of the compound of the general formula VII.

4. The method according to claim 2, wherein the aprotic dipolar solvent is an amide selected from dimethylformamide, dimethylacetamide, diethylacetamide, hexamethylphosphoracidtrisamide or a urea selected from tetramethylurea, 1,3-dimethyltetrahydropyrimidin-2-one and 1,3-dimethylimidazolidinone or a dimethylsulfoxide, and wherein the base is an alkali or alkaline earth hydride selected from sodium hydride, alkali amide selected from sodium amide, sodiummethylacetamide, or an alkali, earth alkali or aluminum alcoholate selected from potassium tert-butylate, sodium methylate, sodium ethylate or aluminum ethylate.

5. A compound formed from the method of claim 2.

6. A pharmaceutical composition comprising a compound of claim 5 and a suitable excipient.

7. A method of treating a cancer in a subject comprising administering to the subject a compound of claim 1.

8. The method of claim 7, wherein the cancer is selected from the group consisting of leukemia, melanoma or mamma carcinoma.

9. A pharmaceutical composition comprising a compound of claim 1 in combination with a suitable excipient.

10. A method of treating a cancer in a subject comprising administering to the subject a compound of claim 5.

11. The method of claim 10, wherein the cancer is selected from the group consisting of leukemia, melanoma or mamma carcinoma.

* * * * *